(12) United States Patent
Wattanakit et al.

(10) Patent No.: US 11,517,885 B2
(45) Date of Patent: Dec. 6, 2022

(54) CATALYST FOR PRODUCING OLEFINS FROM DEHYDROGENATION OF ALKANE AND A METHOD FOR PRODUCING OLEFINS USING SAID CATALYST

(71) Applicant: PTT Global Chemical Public Company Limited, Bangkok (TH)

(72) Inventors: Chularat Wattanakit, Bangkok (TH); Thittaya Yutthalekha, Bangkok (TH); Anawat Thivasasith, Bangkok (TH); Wannaruedee Wannapakdee, Bangkok (TH); Pannida Dugkhuntod, Bangkok (TH); Duangkamon Suttipat, Bangkok (TH)

(73) Assignee: PTT Global Chemical Public Company Limited, Bangkok (TH)

( * ) Notice: Subject to any disclaimer, the term of this patent is extended or adjusted under 35 U.S.C. 154(b) by 141 days.

(21) Appl. No.: 16/759,059

(22) PCT Filed: Nov. 2, 2018

(86) PCT No.: PCT/TH2018/000049
§ 371 (c)(1),
(2) Date: Apr. 24, 2020

(87) PCT Pub. No.: WO2019/088935
PCT Pub. Date: May 9, 2019

(65) Prior Publication Data
US 2020/0338535 A1   Oct. 29, 2020

(30) Foreign Application Priority Data
Nov. 2, 2017 (TH) ................... 1701006520

(51) Int. Cl.
*C07C 5/333* (2006.01)
*B01J 29/035* (2006.01)
*B01J 29/44* (2006.01)
*B01J 37/00* (2006.01)
*B01J 37/02* (2006.01)
*B01J 37/10* (2006.01)
*B01J 35/10* (2006.01)
*B01J 29/46* (2006.01)

(52) U.S. Cl.
CPC ....... *B01J 29/0354* (2013.01); *B01J 29/0356* (2013.01); *B01J 29/44* (2013.01); *B01J 29/46* (2013.01); *B01J 35/1052* (2013.01); *B01J 35/1057* (2013.01); *B01J 35/1061* (2013.01); *B01J 35/1066* (2013.01); *B01J 35/1095* (2013.01); *B01J 37/0018* (2013.01); *B01J 37/0203* (2013.01); *B01J 37/10* (2013.01); *C07C 5/3337* (2013.01); *B01J 37/0201* (2013.01); *B01J 2229/186* (2013.01); *C07C 2523/42* (2013.01); *C07C 2523/755* (2013.01); *C07C 2529/035* (2013.01); *C07C 2529/44* (2013.01); *C07C 2529/46* (2013.01)

(58) Field of Classification Search
CPC .... B01J 29/0354; B01J 29/0356; B01J 29/44; B01J 29/46; B01J 2229/186; B01J 35/1052; B01J 35/0013; B01J 35/065; B01J 35/10; B01J 35/1033; B01J 35/1057; B01J 35/1095; B01J 35/1061; B01J 35/1066; B01J 37/0018; B01J 37/0203; B01J 37/0201; B01J 37/02; B01J 37/10; C07C 2523/42; C07C 2523/755; C07C 2529/035; C07C 2529/44; C07C 2529/46; C07C 2/12; C07C 5/3337; C10G 11/05
USPC ................... 502/4, 60, 74, 77; 585/654, 660
See application file for complete search history.

(56) References Cited

U.S. PATENT DOCUMENTS

| | | | |
|---|---|---|---|
| 5,527,979 A * | 6/1996 | Agaskar ................ C07C 5/3337 585/656 |
| 2013/0059722 A1* | 3/2013 | Tsapatsis ................ B01J 35/10 502/4 |
| 2017/0240431 A1 | 8/2017 | Burton et al. |

FOREIGN PATENT DOCUMENTS

| | | |
|---|---|---|
| EP | 1 194 500 | 4/2002 |
| WO | WO 01/00749 A1 | 1/2001 |

OTHER PUBLICATIONS

Choi et al., "Stable single-unit-cell nanosheets of zeolite MFI as active and long-lived catalysts", Nature, Vo. 461, 2009, pp. 246-249.*
Kim et al. "n-Heptane hydroisomerization over Pt/MFI zeolite nanosheets: Effects of zeolite crystal thickness and platinum location", J. of Catalysis, 301, 2013, pp. 187-197.*
International Search Report dated Feb. 1, 2019 in PCT/TH2018/000049 filed Nov. 2, 2018.
Zhang et al., "Synthesis of Self-Pillared Zeolite Nanosheets by Repetitive Branching," vol. 336, No. 6089, Jun. 29, 2012, 5 pages total, XP055358363.
Xu et al., "On the Synthesis and Adsorption Properties of Single-Unit-Cell Hierarchical Zeolites Made by Rotational Intergrowths," Advanced Functional Materials, vol. 24, No. 2, Jan. 15, 2014, pp. 201-208, XP001588610.

* cited by examiner

Primary Examiner — Elizabeth D Wood
(74) Attorney, Agent, or Firm — Oblon, McClelland, Maier & Neustadt, L.L.P.

(57) ABSTRACT

The present invention relates to a catalyst for producing olefins from dehydrogenation of alkane having 2 to 5 carbon atoms and a method for producing olefins using said catalyst, wherein said catalyst comprises a hierarchical zeolite nanosheet having a silica to alumina ($SiO_2/Al_2O_3$) ratio more than 120 and group X metal(s) in a range of 0.3 to 5% by weight. The catalyst according to the conversion of precursor to yields and high olefins selectivity.

19 Claims, 4 Drawing Sheets

US 11,517,885 B2

CATALYST FOR PRODUCING OLEFINS FROM DEHYDROGENATION OF ALKANE AND A METHOD FOR PRODUCING OLEFINS USING SAID CATALYST

CROSS-REFERENCE TO RELATED APPLICATIONS

The present application is a 35 U.S.C. § 371 National Stage Application of International Patent Application PCT/TH2018/000049, filed Nov. 2, 2018, which is based on and claims the benefit of priority to Thailand Application No. 1701006520, filed Nov. 2, 2017.

TECHNICAL FIELD

The present invention relates to a catalyst for producing olefins from dehydrogenation of alkane and a method for producing olefins using said catalyst.

SUMMARY OF INVENTION

The present invention related to the catalyst for producing olefins from dehydrogenation of alkane having 2 to 5 carbon atoms and a method for producing olefins using said catalyst, wherein said catalyst comprises a hierarchical zeolite nanosheet having a silica to alumina ($SiO_2/Al_2O_3$) ratio more than 120 and group X metal(s) in a range of 0.3 to 5% by weight.

BACKGROUND OF THE INVENTION

It is well known that olefins such as propylene can be prepared from several methods such as metathesis of butane and ethane, transformation reaction of methanol into olefins, and decomposition of hydrocarbon compounds. However, the production process of olefins from hydrogenation of alkanes has been widely used due to non-complex process and cost competitiveness.

Until now, there have been reports in production technology of propylene from hydrogenation of propane such as Catofin Process™ (WO1995023123 and U.S. Pat. No. 5,315,056) from CB&I Lummus. Such process technology uses alumina catalyst containing chromium metal on the support in parallel fixed-bed reactor. In addition, Oleflex Process™ from UOP utilizes alumina catalyst comprising platinum metals and tin on the support in fluidized bed reactor) as disclosed in patent document U.S. Pat. No. 8,563,793.

Apart from the technology described above, there have been disclosed on STAR (Steam Active Reforming) Process™ (U.S. Pat. No. 4,926,005) from UHDE which uses zinc aluminate catalyst comprising platinum metals and tin, and calcium aluminate or magnesium aluminate as binder in fixed-bed reactor. However, chromium metal is classified as a heavy metal and environmental toxicity leading to a limitation applied in industrial. Therefore, there have been continuous attempts to develop catalyst comprising other metals, especially platinum metals and tin, to be efficient for dehydrogenation of alkanes in olefins production.

However, the limitation in propylene selectivity and fast decomposition of the catalyst has been found. This is because the metal sintering that has low reactivity to dehydrogenation can cause the undesired reactions such as cracking reaction and coke formation. Moreover, the use of alumina as the catalyst support results in the undesired reactions and by-products such as methane and ethane.

From all reasons above, there have been attempts to apply zeolite as a support for the noble metal, because zeolite has several good properties such as chemical and heat stability and shape selectivity. Consequently, zeolite has been widely used as the catalyst in petroleum and petrochemical industry. Nevertheless, the conventional zeolite has several limitations such as its acidity which enhances cracking reaction and fast decomposition because of the limitation in mass transfer and very small pores in zeolite structure (angstrom unit). This causes the critical mass transfer condition that obstructs the precursor to be reacted at the catalytic sites, and enhances the decomposition of the catalyst due to the accumulation of coke that clogs the zeolite pores. Moreover, the conventional zeolite is a large zeolite crystal that may be slow down the reactivity of those noble metals when being applied as the support for the noble metal; thus reducing the catalytic efficiency.

Liu Hui et, al. (China Petroleum Processing and Petrochemical Technology, 2013, 15, 54-62) disclosed the ZSM-5 zeolite catalyst comprising platinum metal, tin, and sodium (PtSnNa/ZSM-5) for the hydrogenation of propane by studying the effects of impregnation of the metal to the efficiency of the catalyst. It was found that said catalyst provided not quite high conversion percentage of the precursor to yields.

U.S. Pat. No. 5,516,961 discloses the catalyst of for the dehydrogenation of the light paraffin hydrocarbon, especially the conversion of butane to butane, wherein said catalyst comprising ZSM-5 zeolite having intermediate pore improved by platinum and alkaline metal at the mole ratio of alkaline metal to aluminium in a range about 1 to 5. However, it was found that the selectivity of butane and the conversion percentage of the precursors to yields were not so high.

US 2012/0083641 discloses the catalyst of oxidative dehydrogenation of propane to propylene, wherein said catalyst comprising MCM-41 zeolite improved by vanadium, aluminium, and nickel. However, it was found that said catalyst provided not so high propylene selectivity and conversion percentage of the precursor to yields.

From above-reasons, this invention aims to prepare the hierarchical zeolite nanosheet comprising group X metal(s) for the improvement of zeolite structure to be suitable for its application in olefins production by dehydrogenation of alkanes to provide high conversion percentage of the precursors to yields and high olefins selectivity.

DESCRIPTION OF THE INVENTION

Figure 1:
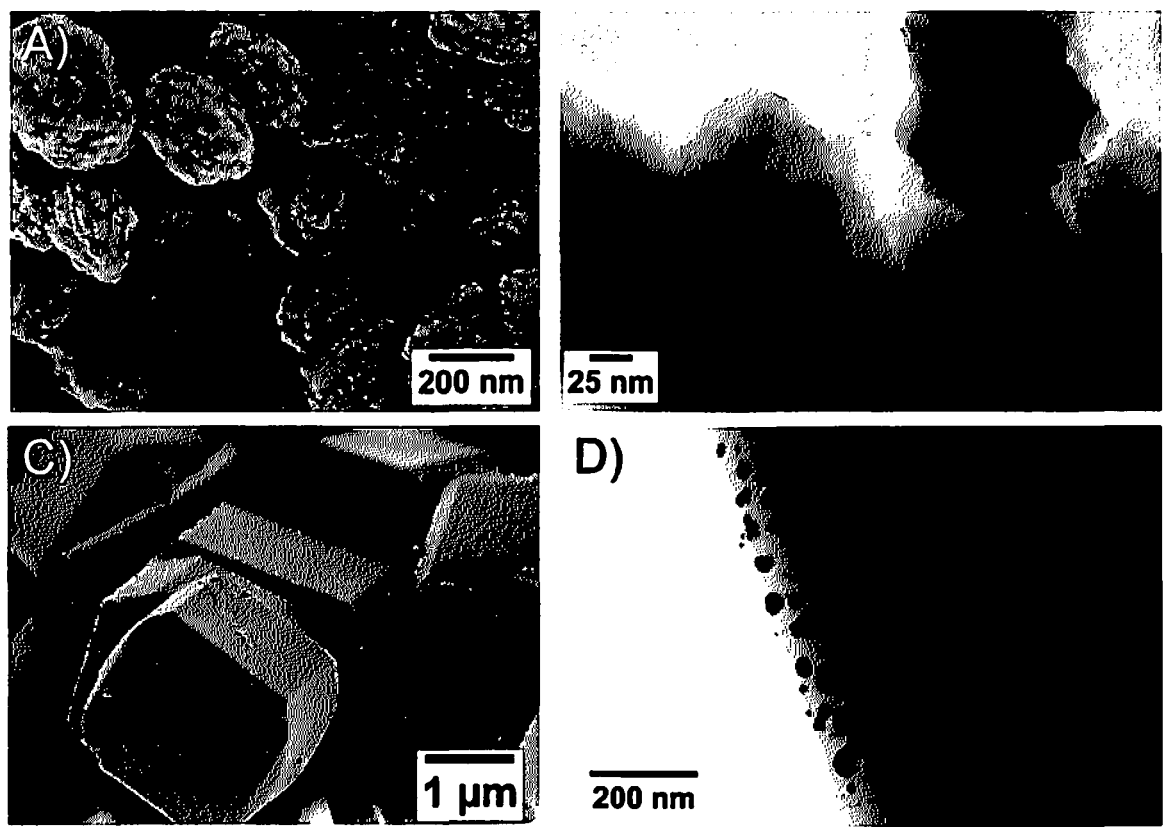
FIGS. 1a) and b) show the scanning electron microscope and transmission electron microscope of the sample according to the invention 2, respectively.
FIGS. 1c) and d) show the scanning electron microscope and transmission electron microscope of the comparative sample B, respectively.

The present invention relates to the catalyst for producing olefins from dehydrogenation of alkane and a method for producing olefins using said catalyst, which will be described according the following embodiments.

Any aspect showed herein is meant to include its application to other aspects of this invention unless stated otherwise.

Technical terms or scientific terms used herein have definitions as by an ordinary person skilled in the art unless stated otherwise.

Any tools, equipment, methods, or chemicals named here mean tools, equipment, methods, or chemicals as being used commonly by an ordinary person skilled in the art unless stated otherwise that they are tools, equipment, methods, or chemicals specific only in this invention.

Use of singular noun or singular pronoun with "comprising" in claims or specification means "one" and including "one or more", "at least one", and "one or more than one".

All compositions and/or methods disclosed and claims in this application aim to cover embodiments from any action, performance, modification, or adjustment without any experiment that significantly different from this invention, and obtain with the objection to utility and resulted as same as the present embodiment according to an ordinary person ordinary skilled in the art although without specifically stated in claims. Therefore, substitutable or similar objection to the present embodiment, including any little modification or adjustment that clearly seen by person skilled in the art should be construed as remains in spirit, scope, and concept of invention as appeared in appended claims.

Throughout this application, term "about" means any number that appeared or showed here that could be varied or deviated from any error of equipment, method, or personal using said equipment or method.

Hereafter, invention embodiments are shown without any purpose to limit any scope of the invention.

The present invention relates to the catalyst for producing olefins from dehydrogenation of alkane having 2 to 5 carbon atoms comprises a hierarchical zeolite nanosheet having a silica to alumina ($SiO_2/Al_2O_3$) ratio more than 120 and group X metal(s) in a range of 0.3 to 5% by weight.

In one embodiment, the hierarchical zeolite nanosheet comprising micropore having a pore diameter in a range of 0.4 to 0.6 nm, mesopore having a pore diameter in a range of 2 to 50 nm, and macropore having a pore diameter greater than 50 nm, in which mesopore and macropore is characterized in 60% or more to total pore volume.

Preferably, micropore having a pore diameter in a range of 0.4 to 0.6 nm, mesopore having a pore diameter in a range of 20 to 40 nm, and macropore having a pore diameter greater than 50 nm, in which the micropore and macropore is characterized in 75% or more to total pore volume.

In one embodiment, group X metal(s) is selected from platinum, palladium, and nickel, preferably is platinum.

Preferably, the catalyst according to the invention comprises the hierarchical zeolite nanosheet having the mole ratio of silica to alumina more than 300, and group X metal in a range of about 0.5 to 2% by weight.

Most preferably, zeolite is silicalite.

In one embodiment, the catalyst according to the invention can be prepared by the following steps:

(a) preparing a solution containing a compound for preparing zeolite and a soft template;

(b) subjecting the mixture obtained from step (a) to hydrothermal process at a determined time and a temperature in order to form said mixture to a hierarchical zeolite; and (c) contacting the hierarchical zeolite obtained from step (b) to group X metal(s) salt solution;

wherein the soft template in step (a) is a quaternary phosphonium salt and group X metal(s) salt in step (c) comprises 0.3 to 5% by weight of group X metal(s) to zeolite.

In one embodiment, the quaternary phosphonium salt is tetraalkylphosphonium salts selected from tetrabutylphosphonium hydroxide and tributyl hexadecyl phosphonium bromide, preferable is tetrabutylphosphonium hydroxide.

In one embodiment, the compound for preparing zeolite is the mixture of alumina selected from aluminum isopropoxide, sodium aluminate, aluminium sulfate, and silica compound selected from tetraethyl orthosilicate, sodium silicate, or silica gel.

Preferably, the compound for preparing zeolite is silica compound selected from tetraethyl orthosilicate, sodium silicate, or silica gel, most preferably tetraethyl orthosilicate.

In one embodiment, step (b) is operated at the temperature in the range of 130 to 180° C.

In one embodiment, step (c) comprises 0.5 to 2% by weight of the ratio of group X metal(s) to zeolite.

In one embodiment, group X metal salt(s) is selected from platinum salt, palladium salt, or nickel salt.

In one embodiment, group X metal salt(s) is selected from chloroplatinic acid, tetraammineplatinum nitrate, palladium nitrate, palladium chloride, fickle chloride, nickel nitrate, and nickel sulfate, preferably tetraammineplatinum nitrate or chloroplatinic acid.

In one embodiment, step (c) may be performed by impregnation.

In one embodiment, the preparation process of said catalyst may be further comprising calcination step.

Drying may be performed by general drying methods using oven, vacuum drying, stirred drying, and rotary evaporation drying.

Calcination may be performed under atmospheric condition for about 1 to 10 hours and the temperature in a range about 400 to 800° C., preferably about 4 to 6 hours and the temperature in a range of about 500 to 600° C.

In another embodiment, the present invention relates to the subjecting of the catalyst according to the invention to dehydrogenation of alkanes having 2 to 5 carbon atoms to produce olefins. Preferably, alkanes are propane or pentane, most preferably propane.

In one embodiment, the dehydrogenation process may be performed wherein the feed line of alkane having 2 to 5 carbon atoms contacted with the catalyst according to the invention at the suitable conditions for the reaction, which may be operated in fixed-bed system, moving bed system, fluidized bed system, or batch system.

The dehydrogenation may be performed at the temperature in the range about 400 to 650° C., preferably in the range about 450 to 550° C., at the pressure under atmospheric pressure to about 3,000 KPa, preferably is in the range about 100 to 500 KPa, and most preferably at the atmospheric pressure.

The weight hourly space velocity (WHSV) of alkane feed line in dehydrogenation is in the range about 1 to 30 hours$^{-1}$, preferably in the range about 3 to 10 hour'.

Generally, any person skilled in this art can adjust the dehydrogenation conditions to be suitable for type and composition of feed line, catalyst, and reactor system.

The following examples are for demonstrating of the embodiments of this invention only, not for limitation of the scope of this invention in any way.

Preparation of the Catalyst

The preparation of the catalyst according to the present invention is prepared by the following method.

The solution comprising aluminium isoproproxide tetraethylorthosilicate was prepared with the determined mole ratio of silica to alumina. Tetrabutylphosphonium hydroxide was used as a template for zeolite. Then, the obtained mixture was subjected to hydrothermal at the temperature about 130 to 180° C. for about 2-4 days in order to convert said mixture into hierarchical zeolite.

Then, the obtained hierarchical zeolite was washed with deionized water until pH of washing liquid was lower than 9. The obtained substance was dried at the temperature about 100-120° C. for about 12-24 hours. The calcination was done in order to remove the template at the temperature about 500-650° C. for about 8-12 hours. The white powder hierarchical zeolite was obtained.

The obtained zeolite was contacted with platinum salt solution by impregnation by adding of about 20 mL of platinum solution into zeolite obtained from about 1 g of the above processes, wherein the ratio of platinum to zeolite was about 1% by weight. The obtained mixture was stirred for about 6 to 12 hours, and dried with rotary evaporator and calcinated at the temperature about 550° C. for about 5 to 10 hours.

Comparative Sample Cat A (ZSMS-con-120)

The obtained ZSM-5 zeolite with mole ratio of silica to alumina about 120 that had been synthesized according to the method disclosed by Hensen et al., (Catalysis Today, 2011, 168, 96-111) was brought to contact with platinum salt solution by method described above.

Comparative Sample Cat B (Silicalite-con)

The ZSM-5 zeolite with that had been synthesized according to the method disclosed by Hensen et al., (Catalysis Today, 2011, 168, 96-111) without alumina as its composition was brought to contact with platinum salt solution by method described above.

Sample According to the Invention Cat 1 (ZSMS-NS-120)

The sample according to the invention Cat 1 was prepared by the method according to the invention as described above using mole ratio of silica to alumina of 120 was brought to contact with platinum salt solution by method described above.

Sample According to the Invention Cat 2 (Silicalite-NS)

The sample according to the invention Cat 2 was prepared by the method according to the invention as described above without alumina used in the preparation step was brought to contact with platinum salt solution by method described above.

Dehydrogenation Testing

The dehydrogenation testing may be performed by the following conditions.

The dehydrogenation was operated in fixed-bed reaction using about 0.2 g of the catalyst. Prior to the reaction, the catalyst was contacted with about 2-10% by volume of hydrogen in nitrogen with the flow rate about 10 to 50 mL/min for about 1 to 3 hours. Then, alkane having 2 to 5 carbon atoms was fed with flow rate about 1-3 g/hour. The reaction was operated at the temperature about 450-550° C. at the atmospheric pressure and the weight hourly space velocity (WHSV) about 5 hour$^{-1}$.

Then, the reaction was followed by measuring the change of precursor and the generation of each composition after catalyzing at each time by gas chromatography connected to the outlet of the fixed-bed reactor using flame ionization detector (FID) as the detector and the HP-AL/S and GASPRO capillary column for the analysis of each said composition Table 1 shows the physical properties of the hierarchical zeolite nanosheet according to the invention and the comparative sample. From the table, it was found that zeolite prepared from the invention comprises of micropore, mesopore, and macropore, wherein the mesopore and macropore was more than 60% of total pore volume. The content of zeolite prepared from the invention is significantly greater than conventional zeolite. This shows the hierarchical porous. Moreover, in order to show crystalline structure, the obtained substance was tested by scanning electron microscope (SEM) and transmission Electron Microscopy (TEM) as the results shown in FIG. 1. The zeolite according to the invention was a thin nanosheet with particle size in a range of about 120-200 nm. It was also found that the hierarchical zeolite nanosheet had significantly smaller platinum particle than the conventional zeolite support, whereas the conventional zeolite had large and irregular platinum particle size when prepared under the same testing condition.

Figure 2:
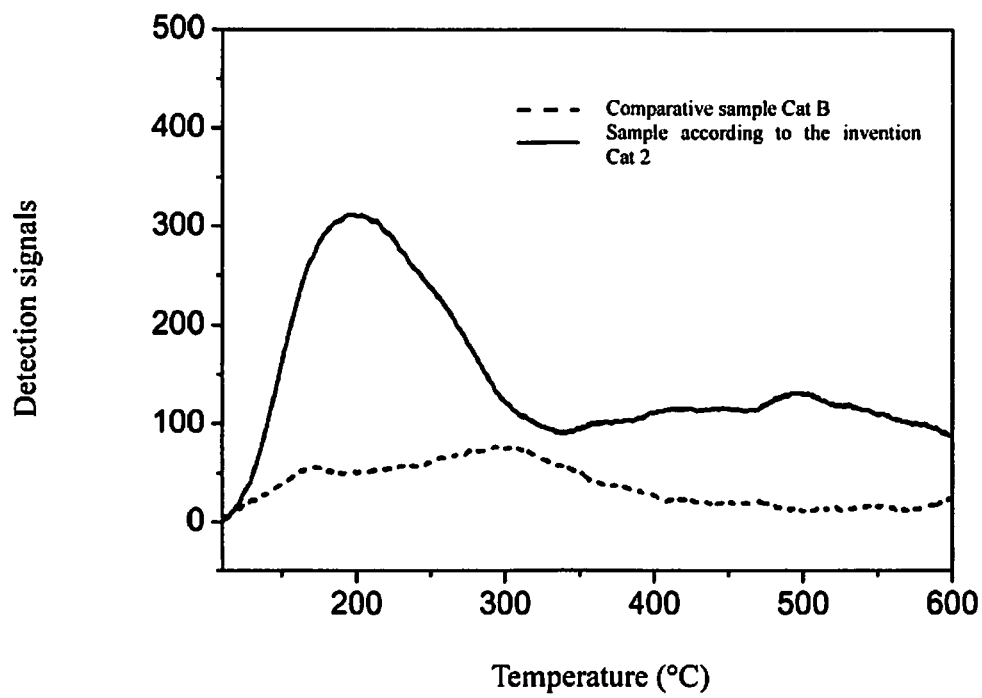
FIG. 2 shows the acidity property of the sample according to the invention 2 and the comparative sample B using ammonia temperature programmed desorption technique.

FIG. 2 shows the acidity property of the hierarchical zeolite nanosheet according to the invention and the conventional zeolite using ammonia temperature programmed desorption technique in acidity testing. It was found that the zeolite according to the invention significantly reduced strong acid sites as it can be seen from the peak area at the temperature in a range of 300 to 500° C. Said result affected in reducing side reactions, including coke reaction and cracking reaction, thus decreasing by-product formation.

TABLE 1

Specific surface area and hierarchical property of zeolites

| Sample | Specific surface area ($S_{BET}$) (m$^2$/g) | Specific external surface area ($S_{ext}$) (m$^2$/g) | Total pore volume ($V_{total}$) (cm$^3$/g) | Micropore volume ($V_{micro}$) (cm$^3$/g) | Macropore and mesopore percentage (%) |
|---|---|---|---|---|---|
| Sample according to the invention Cat 2 | 399 | 104 | 0.56 | 0.12 | 78 |
| Comparative sample Cat B | 374 | 52 | 0.25 | 0.13 | 48 |

Note:
BET (specific surface area);
$S_{ext}$ (external surface area);
$V_{total}$ (total pore volume);
$V_{micro}$ (micropore volume);
$V_{meso+macro}$ (macropore and mesopore volume)

To study the effect of the hierarchical zeolite nanosheet structure to the performance of said zeolite as the dehydrogenation catalyst, the zeolites according to the invention were used to study with the comparative samples using the conventional zeolite as shown in FIG. 3 to FIG. 6.

Figure 3:
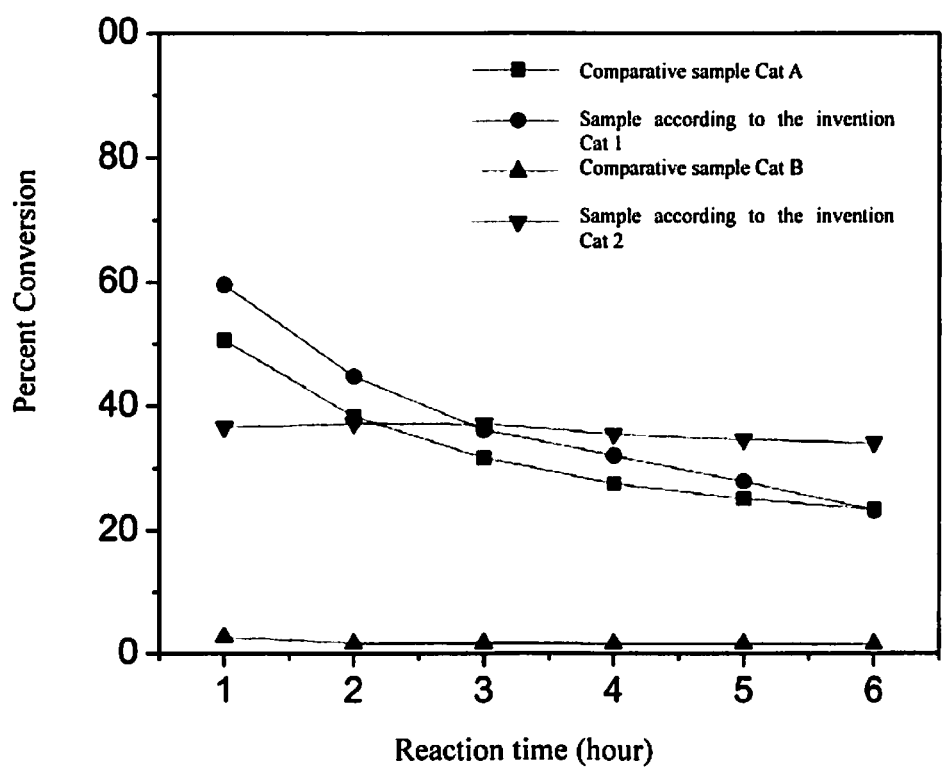
FIG. 3 shows the percent conversion of zeolite sample according to the invention and the comparative sample for hydrogenation of propane.
Figure 4:
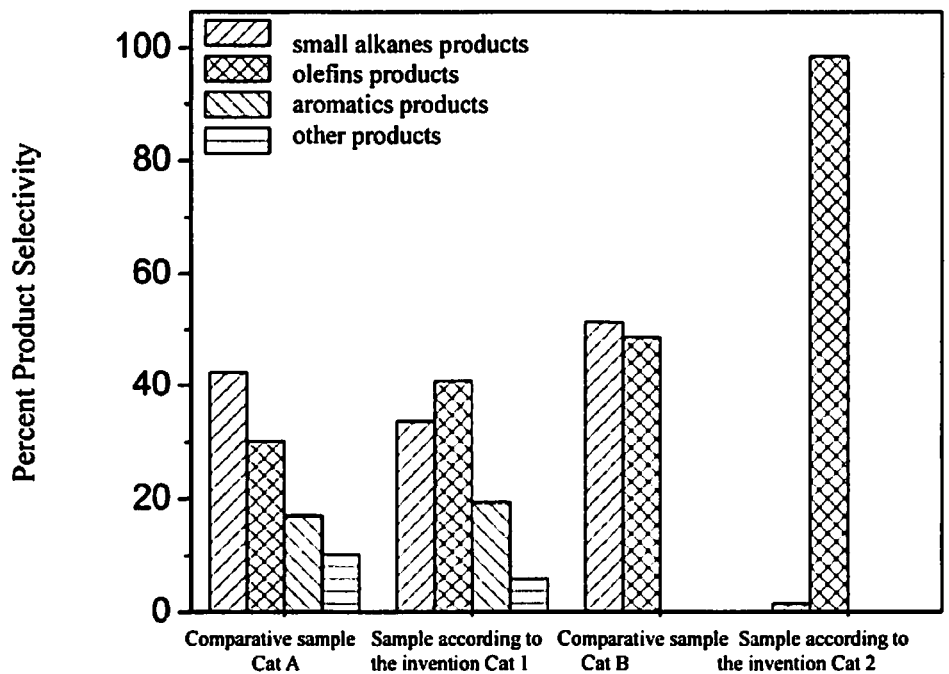
FIG. 4 shows the percent product selectivity of zeolite sample according to the invention and the comparative sample for hydrogenation of propane.

FIG. 3 and FIG. 4 shows the performance of zeolite as the dehydrogenation catalyst of propane. It was found that the sample according to the invention Cat 1 and Cat 2 showed better conversion of propane, higher propylene selectivity and better stability than the conventional zeolite.

Figure 5:
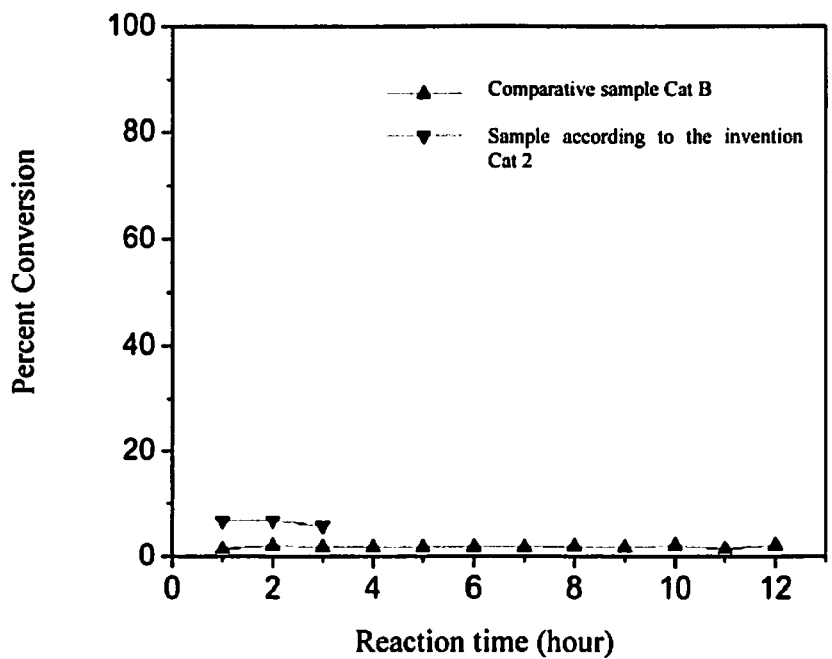
FIG. 5 shows the percent conversion of zeolite sample according to the invention and the comparative sample for hydrogenation of pentane.
Figure 6:
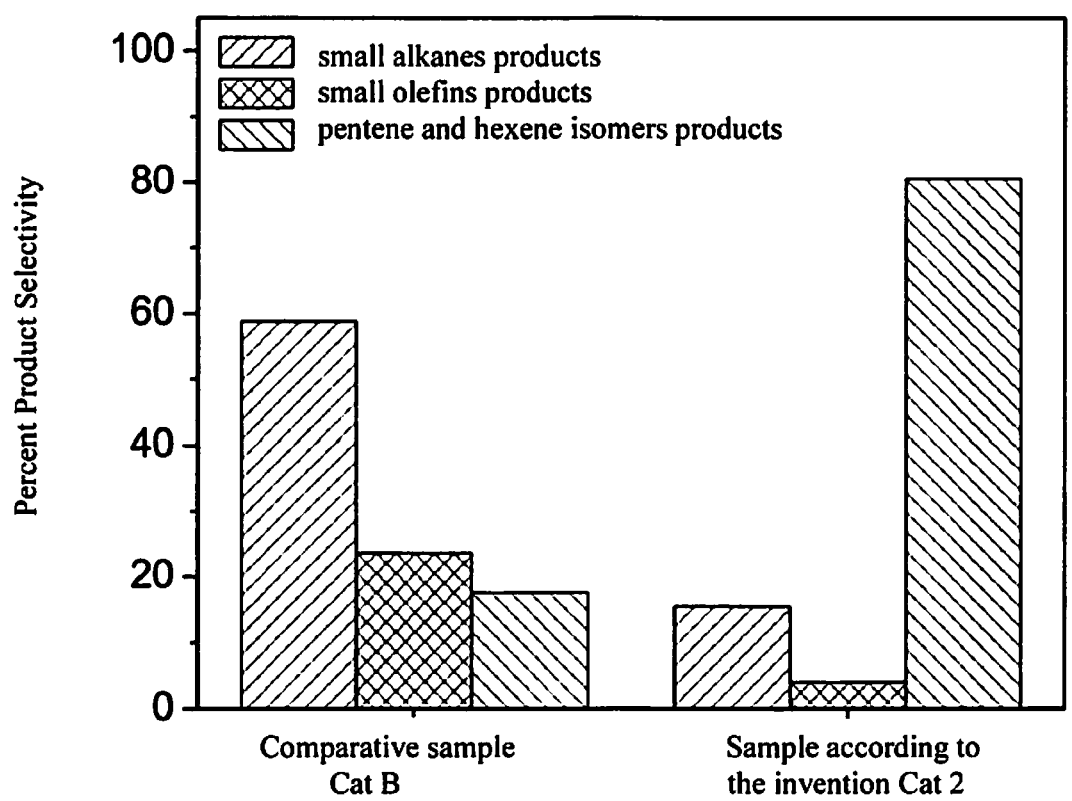
FIG. 6 shows the percent product selectivity of zeolite sample according to the invention and the comparative sample for hydrogenation of pentane.

FIG. 5 and FIG. 6 shows the performance of zeolite as the dehydrogenation catalyst of pentane. It was found that the sample according to the invention Cat 2 showed better conversion of pentane and higher propylene selectivity than the conventional zeolite.

From the results above, it can be said that the hierarchical zeolite nanosheet catalyst according to the invention provided high conversion and high olefins selectivity for the dehydrogenation of alkane containing 2 to 5 carbon atoms as indicated in the objectives of this invention.

BEST MODE OF THE INVENTION

Best mode of the invention is as provided in the description of the invention.

The invention claimed is:

1. A catalyst for producing olefins from dehydrogenation of an alkane having 2 to 5 carbon atoms, the catalyst comprising:
    a hierarchical zeolite nanosheet having a silica to alumina ($SiO_2/Al_2O_3$) molar ratio of 120 or greater,
    wherein the hierarchical zeolite nanosheet comprises one or more metals of group X of the periodic table in a range of 0.3 to 5 wt % relative to a total weight of hierarchical zeolite nanosheet, and
    wherein the hierarchical zeolite nanosheet has
        micropores having a pore diameter in a range of 0.4 to 0.6 nm,
        mesopores having a pore diameter in a range of 2 to 50 nm, and
        macropores having a pore diameter greater than 50 nm, and
    wherein the mesopores and macropores contribute to 60% or more of the total pore volume as measured by $N_2$ adsorption/desorption using BJH (Barrett, Joyner, and Halenda) model.

2. The catalyst of claim 1, wherein the mesopores have a pore diameter in a range of 20 to 40 nm, and
    wherein the mesopores and macropores contribute to 75% or more of the total pore volume.

3. The catalyst of claim 1, wherein the one or more metals of group X of the periodic table is selected from the group consisting of platinum, palladium, and nickel.

4. The catalyst of claim 3, wherein the one or more metals of group X of the periodic table is platinum.

5. The catalyst of claim 1, wherein the silica to alumina molar ratio is more than 300.

6. The catalyst of claim 1, wherein the hierarchical zeolite nanosheet is silicalite.

7. The catalyst of claim 1, which comprises the one or more metals of group X of the periodic table at a weight percentage of 0.5 to 2 wt % relative to a total weight of the hierarchical zeolite nanosheet.

8. A method for preparing the catalyst of claim 1, comprising:
    preparing a mixture containing a soft template and a compound for preparing a zeolite;
    subjecting the mixture to a hydrothermal process at a temperature in a range of 130 to 180° C. in order to form a hierarchical zeolite; and
    contacting the hierarchical zeolite with a salt solution of a metal salt of the one or more metals of group X of the periodic table;
    wherein the soft template is a quaternary phosphonium salt.

9. The method of claim 8, wherein the compound for preparing a zeolite is a mixture of an aluminum compound and a silica compound,
    wherein the aluminum compound is selected from the group consisting of aluminum isopropoxide, sodium aluminate, and aluminum sulfate, and
    wherein the silica compound is selected from the group consisting of tetraethyl orthosilicate, sodium silicate, and silica gel.

10. The method of claim 8, wherein the compound for preparing a zeolite is a silica compound selected from the group consisting of tetraethyl orthosilicate, sodium silicate, and silica gel.

11. The method of claim 8, wherein the quaternary phosphonium salt is a tetraalkylphosphonium salt selected from the group consisting of tetrabutylphosphonium hydroxide and tributyl hexadecyl phosphonium bromide.

12. The method of claim 11, wherein the quaternary phosphonium salt is tetrabutylphosphonium hydroxide.

13. The method of claim 8, wherein the salt solution comprises the one or more metals of group X of the periodic table at a weight percentage of 0.5 to 2 wt % relative to a total weight of hierarchical zeolite.

14. The method of claim 8, wherein the metal salt is selected from the group consisting of a platinum salt, a palladium salt, and a nickel salt.

15. The method of claim 8, wherein the metal salt is selected from the group consisting of chloroplatinic acid, tetraammineplatinum nitrate, palladium nitrate, palladium chloride, nickel chloride, nickel nitrate, and nickel sulfate.

16. The method of claim 15, wherein the metal salt is tetraammineplatinum nitrate or chloroplatinic acid.

17. The method of claim 8, wherein the contacting is performed by impregnation.

18. A process for producing olefins, comprising contacting an alkane with the catalyst of claim 1.

19. The process of claim 18, which uses a temperature in a range of 450 to 550° C., and
    wherein the alkane is selected from the group consisting of propane and pentane.

* * * * *